United States Patent [19]

Karimi et al.

[11] Patent Number: 5,061,424

[45] Date of Patent: Oct. 29, 1991

[54] METHOD FOR APPLYING A LUBRICIOUS COATING TO AN ARTICLE

[75] Inventors: Houshang Karimi, Centerville; Mutlu Karakelle, Spring Valley; Robert A. Taller, Centerville, all of Ohio

[73] Assignee: Becton, Dickinson and Company, Franklin Lakes, N.J.

[21] Appl. No.: 643,639

[22] Filed: Jan. 22, 1991

[51] Int. Cl.$^5$ ............................................. B29C 47/06
[52] U.S. Cl. ................................. 264/171; 264/130; 264/173; 264/300; 264/331.19; 264/209.1
[58] Field of Search ............... 264/171, 173, 300, 130, 264/514, 150, 331.19, 209.1

[56] References Cited

U.S. PATENT DOCUMENTS

| | | |
|---|---|---|
| 4,062,834 | 12/1977 | Gilding et al. . |
| 4,100,309 | 7/1978 | Micklus et al. . |
| 4,211,741 | 7/1980 | Ostoich ............................ 264/173 |
| 4,299,256 | 11/1981 | Bacehowski et al. ............. 264/173 |
| 4,373,009 | 2/1983 | Winn . |
| 4,485,062 | 11/1984 | Dawes et al. ..................... 264/171 |
| 4,551,292 | 11/1985 | Fletcher et al. .................. 264/173 |
| 4,642,267 | 2/1987 | Creasy et al. . |
| 4,720,521 | 1/1988 | Spielvogel et al. . |
| 4,767,414 | 8/1988 | Williams et al. . |
| 4,880,592 | 11/1989 | Martini et al. .................... 264/514 |
| 4,904,431 | 2/1990 | O'Maleki ........................ 264/173 |
| 4,952,359 | 8/1990 | Wells .............................. 264/173 |
| 4,963,306 | 10/1990 | Weldon ........................... 264/150 |

OTHER PUBLICATIONS

Nagoaka et al., *Biomaterials,* 419, (1990).
*Petrothene* ® *Polyolefins—A Processing Guide,* Fifth Edition, 1986, p. 73 et seq., USI Chemicals, Division of National Distillers and Chemical Corp.
Michaeli, *Extrusion Dies,* p. 210, et seq., Hanser Publishers, New York, New York, 1984.
*Handbook of Water Soluble Gums and Resins,* R. L. Davidson, Ed., McGraw-Hill 1980, pp. 21.1–21.2.

Primary Examiner—Jeffery Thurlow
Attorney, Agent, or Firm—Richard E. Brown

[57] ABSTRACT

A composition which includes polyvinylpyrrolidone and a polyurethane is melt processed to give a shaped article. The melt processing may be a coextrusion with a substrate polymer to give a shaped article having the composition coated on the surface thereof. The article surface is lubricious when contacted with water.

16 Claims, No Drawings

METHOD FOR APPLYING A LUBRICIOUS COATING TO AN ARTICLE

BACKGROUND OF THE INVENTION

1. Field of the Invention

This invention relates to lubricated surfaces. More particularly, the invention relates to a method for coating a surface with a lubricious and biocompatible composition.

2. Background

Many articles, devices and products require a lubricated surface. In the medical instrumentation and diagnostic field, simple sensing devices such as, for example, thermometers and needles, or electrode components of complex monitoring apparatuses, must be inserted into a body cavity or through the skin and at a later time withdrawn. Patient treatment often includes catheterization procedures or nutrition delivery systems, most of which involve invasive techniques. In all such cases, effective lubrication which is stable throughout both the insertion and withdrawal stages of the procedure contributes greatly to patient comfort.

Many medical devices are fabricated from glass or polymeric materials such as polypropylene, polyvinyl chloride (PVC), polytetrafluoroethylene (PTFE) and polyurethane (PU). Such materials are for the most part inherently nonlubricious. A variety of approaches to introduce lubricity have been advanced. Simple coatings of lubricants such as mineral oils or silicones to glass or polymeric surfaces are generally unsatisfactory because the surface energy is too low and the lubricant tends to migrate or "bead." A method to overcome migration of silicone lubricants is described by Williams et al. in U.S. Pat. No. 4,767,414. A surface to be lubricated is coated with silicone oil and both the surface and oil are subjected to an ionizing plasma.

Spielvogel et al., in U.S. Pat. No. 4,720,521 teaches adherence of a lubricating composition to a surface. The composition includes a polysiloxane lubricant entrapped in a mixture of a plurality of reactive silicone components which, on curing, adhere to the surface.

Thermoplastic polyurethanes prepared from polyisocyanates, high molecular weight polyetherglycols, and low molecular weight diols and diamines as chain extenders are conventionally referred to as polyetherurethanes, and this term will be used in this disclosure for polyurethanes having a polyether backbone.

Polyetherurethane compositions develop microdomains conventionally termed hard segment domains and soft segment domains and are often referred to as segmented polyurethanes. They are (AB)n type block copolymers, A being the hard segment and B the soft segment. The hard segment domains form by localization of the portions of the copolymer molecules which include the isocyanate and extender components whereas the soft segment domains form from the polyether glycol portions of the copolymer chains. The phase separated microdomain structure forms if the hard segments of polyetherurethane chain are a certain size. A long hard segment promotes the phase separated microdomain structure. Conversely, non-extended formulations (those lacking an extender) have very short hard segments and minimum phase separated microdomain structure. The hard segment is crystalline and provides physical crosslinking and reinforcement. The polyether glycol soft segment is mostly in a rubbery state and provides elasticity. Therefore, polyetherurethanes are thermoplastic elastomeric materials. A wide range of physical properties can be obtained by altering the relative ratios of the hard and soft segments. The elasticity, toughness and other desirable properties of polyetherurethanes are the result of their phase separated microdomain structure.

Elastomeric segmented polyurethanes have particular advantages for fabrication of medical devices, as discussed by Gilding et al. in U.S. Pat. No. 4,062,834. However, polyurethanes have limited inherent lubricity.

Micklus et al. overcomes this problem in U.S. Pat. No. 4,100,309 with a lubricious polyurethanepolyvinylpyrrolidone (PVP) interpolymer coating which may be applied to a polymeric article by dipping the article into a solvent solution of polyurethane and a polyisocyanate to give an isocyanate-containing prepolymer on the article surface and dipping the prepolymer-coated article into a solution of PVP. In U.S. Pat. No. 4,373,009 to Winn, a substrate surface is primed with a polyisocyanate as shown by Micklus et al., and the isocyanate groups are covalently bonded to active hydrogens of a hydrophilic copolymer, such as a copolymer of PVP and acrylamide. A coating which is stable and resistant to removal, in contrast to the prior art coating, is claimed. U.S. Pat. No. 4,642,267 to Creasy et al. describes alloys or blends of PVP and polyester polyurethanes lacking both free isocyanate groups and chain extenders. The patented blends are processed from solvent solutions or aqueous dispersions.

Nagoaka et al., in *Biomaterials*, 419, (1990), disclose dipping a medical device containing amino groups on its surface into a solvent solution of a copolymer of PVP and glycidyl acrylate. The amino groups react with the epoxy group of the glycidyl acrylate to covalently bond the PVP-containing copolymer to the device surface. The surface becomes slippery when wet.

In allowed conceding application Ser. No. 347,133 of common assignee herewith now U.S. Pat. No. 4,990,357, a blend of a hydrophilic polyetherpolyurethane (HPEU) and PVP is dip coated onto a polymeric medical article to give stable coating which is lubricious when wet.

The above disclosures have advanced the art of rendering surfaces lubricious but suffer the disadvantage of requiring solvent dip coating for application of the PU-PVP coating. Solvent based coating has been required because PVP has a high melt viscosity due to high hydrogen bonding between PVP molecules. Because of the high viscosity thermoplastic operations have heretofore been impractical for application of PVP. There remains a need for a method to apply a PVP coating which is instantly lubricious, easily applied and strongly adherent so as to remain on the substrate to which it is applied with no tendency to wash off or separate as solid flakes on prolonged contact with liquids.

SUMMARY OF THE INVENTION

A method to prepare an article having a surface which absorbs water and becomes lubricious comprises melt fabricating a composition including PVP. In this disclosure, the term fabricating includes extruding and molding.

In one embodiment of the invention, a melt of the composition is extruded or molded to give a shaped article. In a second embodiment of the invention, a melt of the composition and a melt of a substrate polymer are coextruded to give a shaped article having a coating of the composition on the surface of the substrate polymer. In still another embodiment of the invention, a melt of the composition is extrusion coated onto a surface of a preformed shaped article of the substrate polymer.

The composition to be melt fabricated by the method of the invention includes a uniform blend of the PVP and a PU, preferably an HPEU. Preferred compositions are blends of PVP and a diol extended HPEU which includes polyethyleneoxide as the soft segment. The most preferred composition has a hard segment content of about 35 to 55%.

In accordance with the invention, the surface of a medical article of the composition is rendered instantly lubricious when the composition is wetted with an aqueous liquid or water. When coated onto the substrate polymer, the composition adheres firmly to the surface of the article through the HPEU component. The PVP component is trapped in the HPEU matrix as a result of strong hydrogen bonding and migrates slowly to the surface of the HPEU when the composition is in contact with the liquid. The mobile PVP on the surface is believed to account for the outstanding lubricity of articles fabricated with the composition. Because the migration is slow, the article remains lubricious for prolonged times.

In particular, the inclusion of the elastomeric segmented HPEU provides hard segments through which exceptionally strong hydrogen bonding to the article surface are formed so that there is no tendency for the coating to separate from the surface, even under conditions of exposure to flowing liquids, as blood. Further, the elastomeric segmented HPEU having phase separated microstructure contributes to a surface having a high level of biocompatibility, in particular excellent blood compatibility and thus very low thrombogenicity and very low toxicity.

By the melt processing method of the invention, advantage may be taken of the outstanding lubricity provided by PVP without resort to the solvent based methods of the prior art. While solvent based methods are adequate for laboratory or low volume industrial processes, they are very costly in large scale operations. The melt processing method disclosed herein provides ease of processing/manufacturing using little plant floor space and little capital expenditures. Further, there is no need for solvent removal/recovery and therefore no danger due to exposure of plant personnel to toxic materials. Significant savings in cost and reduction in environmental hazard is achieved.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In one embodiment of the present invention, a method is provided for coating a polymeric substrate with a PVP-containing composition which gives a stable lubricious substrate surface when the substrate comes into contact with a liquid. A variety of substrates is contemplated to be coated with the PVP composition of the invention. Preferred substrates are thermoplastic and may be polyester, polyamide, PVC, polyacrylate, polystyrene, latex rubber and, most preferably PU. Most preferably, a thermoplastic PVC or PU substrate polymer is coextruded with the PVP composition of the invention.

HPEUs suitable for use as the base component of the composition include three essential components, a diisocyanate, a polyether glycol and a chain extender. Suitable diisocyanates are aromatic diisocyanates such as MDI, alicyclic diisocyanates such as isophorone diisocyanate and 4,4'-dicyclohexylmethane diisocyanate, and aliphatic diisocyanates, as, for example, hexamethylene diisocyanate. The most preferred diisocyanate is MDI.

The polyether glycol component may be PEG, alone or mixed with polypropyleneoxide glycol or polytetramethyleneoxide glycol. The preferred polyol is PEG having a molecular weight of from about 600 to 8,000, or a mixture containing 50% or more by weight thereof. The most preferred polyether glycol is a PEG having an average molecular weight of 1000 to 1450.

The chain extender may be water and/or a low molecular weight branched or unbranched diol, diamine or aminoalcohol of up to 10 carbon atoms or mixtures thereof. Representative nonlimiting examples of chain extenders are BDO; ethylene qlycol; diethylene qlycol; triethylene qlycol; 1,2-propanediol; 1,3-propanediol; 1,6-hexanediol; 1,4-bis-hydroxymethyl cyclohexane, hydroquinone dihydroxyethyl ether, ethanolamine, ethylenediamine and hexamethylenediamine. Preferred chain extenders are 1,6-hexanediol, ethylenediamine hexamethylenediamine and, most preferably, BDO.

The percentages of the components may be such that the hard and soft segments of the composition may be from about 25 to 60 and from about 40 to 75, preferably from about 30 to 50% and 50 to 70% respectively of the total weight of the formulation. From these percentages and ratios, suitable proportions of the components may readily be calculated. Representative elastomeric segmented HPEU base components are listed in Table I of Example I below.

The HPEU base component of the composition may be prepared by solution or bulk synthesis methods. Example I provides typical procedures, however, various modifications of this conventional procedure are well-known to those skilled in the art. Alternatively, the HPEU may be prepared by conventional emulsion polymerization, in water, to give an HPEU latex.

A feature of the method for preparing the HPEU formulations of the invention is that the polymers are prepared from the components without adding a polymerization catalyst. Conventional catalysts in the art, for example, organometallic compounds such as dibutyl tin dilaurate, are leachable and may cause deleterious effects in blood-contacting elements fabricated from prior art catalyst-containing HPEU. By avoiding use of a catalyst, HPEUs of the invention are purer and potentially less toxic than those of the prior art.

The PVP of the invention may be of any suitable molecular weight preferably about 10,000 to 1,000,000.

Since PVP does not react with any of the HPEU components, the composition may be prepared by adding the PVP to the recipe described above for HPEU synthesis. Alternatively, the components of the composition may be blended by melt compounding, such as in a Banbury mixer, or with a single or twin screw extruder.

In a preferred method for preparing the composition, the HPEU and PVP are mixed in a suitable solvent wherein the ratio of HPEU to PVP may be about 99:1 to 30:70 by weight. The preferred ratio is about 50:50 by weight. Suitable solvents are dimethylformamide, dimethylacetamide (DMAC) and N-methylpyrrolidone. These high boiling solvents may be used alone but preferably are mixed with a low boiling solvent such as tetrahydrofuran (THF), methylene chloride or methylethylketone. Most preferably, a solvent mixture containing a 3:2 ratio of DMAC to THF is used. The composition may be about 1 to 20, preferably about 4 to 12% by weight in the solvent.

It is evident that, if the HPEU is prepared by emulsion polymerization as described above, the water may serve as the solvent and the PVP merely added thereto.

Depending on the intended use, other components may be incorporated into the coating composition of the invention in order to achieve particular properties. For example additives such as flow aids, flatting agents, plasticizers, heat stabilizers and surface cure modifiers may be added to the HPEU formulation prior to prepolymer formation, prior to conversion of the prepolymer to the HPEU, or preferably directly to the solvent solution of the components. Such additives and their use to modify polymer properties are conventional and well known to those skilled in the art.

Particularly preferred is addition of an antimicrobial agent to the coating composition. Any antimicrobial agent which is substantially stable to thermoplastic processing conditions and which may be released slowly from the coating may be used. Exemplary of suitable antimicrobial agents are chlorohexidene and propylparaben. The quantity of antimicrobial agent to be added may be from about 1 to 10, preferably 2 to 6 weight percent.

The solvent may then be removed to leave a homogeneous blend of the HPEU, PVP and any additive which is ready for extrusion. Any conventional procedure or equipment may be used for solvent removal, such as spray coating, roller drying or precipitation in a nonsolvent such as acetone or carbon tetrachloride. Preferably the solvent solution is cast into a film and the solvent removed from the film by any conventional technique. Most preferably, the cast film is heated in a convection oven at a temperature from ambient to about 70° C. Reduced pressure may be used to aid solvent removal. The resulting homogeneous blend may be chipped or pelletized prior to melt processing.

The blend may be molded or extruded to give an article formed wholly of the composition, or the composition may be coextruded with a substrate polymer using any conventional and commercially available coextrusion equipment. Suitable coextrusion apparatus may be purchased, for example, from Genca Cable Company, Clearwater, Fla., or from Wayne Machine and Die Company, Totowa, N.J., or, if desired, custom coextrusion apparatus an be designed for fabrication of any specific article of the invention.

Alternatively, the composition may be extrusion coated onto a preshaped polymeric article. Extrusion coating is a conventional process in which a melt of thermoplastic material is metered through a die directly onto a solid, continuous, shaped surface.

General and specific descriptions of equipment and processing conditions for extrusion coating may be found in *Petrothene® Polyolefins—A Processing Guide*, Fifth Edition, 1986, page 73 et seq. published by USI Chemicals, Division of National Distillers and Chemical Corp. A discussion of dies and equipment suitable for extrusion coating of wires wherein a melt flows around a hollow mandrel through which a wire is passed is given by Michaeli in *Extrusion Dies*, Page 210, et sec., Hanser Publishers, New York, N.Y. (1984).

The coating of the invention may be from about 2.5 to 500, preferably about 2.5 to 125 microns thick.

The composition of the invention is dry and nonsticky to the touch until wet with a liquid, at which time it develops a slippery lubricious feel. It is believed, although as yet unsubstantiated, that the composition of the invention includes strong hydrogen bonding between the HPEU and PVP chains which effectively reduces the bonding between PVP molecules and thereby makes thermoplastic processing of the PVP possible. The chains of PVP are believed to be substantially trapped in the HPEU base polymer without actually being chemically linked thereto. This arrangement of the two polymers provides the composition with the mechanical strength and bonding capability of segmented PUs yet leaves the PVP molecules unattached so that slow diffusion to the surface may take place.

The composition of the invention is particularly useful when fabricated into or coated onto medical devices, most preferably devices having the shape of a rod or tubing. For example, a catheter coated with the composition becomes instantly lubricious when it comes into contact with water or a body fluid such as blood and thereby contributes greatly to the comfort of a patient undergoing catheterization. An extruded rod in the form of a guidewire becomes lubricious when wet and slides inside of a catheter. One skilled in the art will immediately recognize other medical devices, such as nutrition delivery systems, cannulas, needles, thermometers, urethral catheters and various components of medical monitoring apparatuses which may advantageously be coated with or fabricated from the composition of the invention.

A preferred procedure for preparing the composition of the invention is given in Example II. Examples III and IV give typical extrusion and coextrusion procedures.

The composition of the invention is substantially dry until contacted with a liquid whereupon it is instantly rendered lubricious. Lubricity may be determined by measuring the coefficient of friction using the Instron Model 1122 Universal Testing Machine by the procedure described in Example V.

The following examples are given to further illustrate the invention but are not to be considered as limitative thereof.

EXAMPLE I

Bulk Synthesis of HPEU

PEG was dried at 60° to 70° C. under vacuum (4-6 mm Hg) for 4 to 6 hours to remove moisture. Water content (Carl Fisher titration) and polyol hydroxyl number (phthalic anhydride pyridine method) were determined to adjust formulation stoichiometry. MDI was filtered to remove any reacted diisocyanate and vacuum stripped (4-6 mm Hg) for 2 to 4 hours. The stoichiometric amounts of PEG and BDO were placed in the polymerization vessel and degassed at 60° for 30 minutes. Then, the stoichiometric amount of MDI (1.02 index) was added and the mixture stirred vigorously until the polymerization temperature reached about 85° to 90° C. The polymer was discharged and postcured at 125° C. for 30 minutes.

Solution Synthesis of HPEU

Solution polymerization at 25% total solids was performed in DMAC under a nitrogen atmosphere. PEG was dried at 60° to 70° C. under vacuum (4–6 mm Hg) for 4 to 6 hours to remove moisture. Water content (Carl Fisher titration) and polyol hydroxyl number (phthalic anhydride pyridine method) were determined to adjust formulation stoichiometry. MDI was filtered to remove any reacted diisocyanate and vacuum stripped (4–6 mm Hg) for 2 to 4 hours. Stoichiometric amounts of PEG and BDO were placed in the polymerization vessel and degassed at 60° C. for 30 minutes. Two thirds of the total solvent used (DMAC) was added to the PEG-extender mixture. The stoichiometric (1.02 Index) amount of MDI was dissolved in the remaining DMAC and the solution was added dropwise to the polymerization vessel. The polymerization medium was maintained at 60° to 70° C. and constantly stirred. A polymerization time of four hours at 60° to 70° C. was sufficient for adequate formation.

TABLE I

Typical HPEUs of the Invention

| HPEU NO. | HS CONTENT (% WT) | POLYETHER TYPE | NUMBER OF EQUIVALENTS OF | | |
|---|---|---|---|---|---|
| | | | MDI | BDO | PEG |
| 1 | 30 | PEG 1450 | 1.02 | 0.506 | 0.494 |
| 2 | 35 | PEG 1450 | 1.02 | 0.597 | 0.403 |
| 3 | 40 | PEG 1450 | 1.02 | 0.667 | 0.333 |
| 4 | 45 | PEG 1450 | 1.02 | 0.738 | 0.262 |
| 5 | 50 | PEG 1450 | 1.02 | 0.772 | 0.228 |
| 6 | 55 | PEG 1450 | 1.02 | 0.821 | 0.179 |
| 7 | 60 | PEG 1450 | 1.02 | 0.845 | 0.155 |

EXAMPLE II

Preparation of Composition for Extrusion

The HPEU of Example I was dissolved in a 3:2 by weight mixture of DMAC and THF and the desired amount of PVP (K-90, Aldrich) was added. The solution was stirred until homogeneous to give a clear solution which could be stored for months without decomposition.

The solution was cast into a film, the film was dried in a convection oven at about 70° C., and the blend was chipped into pellets.

EXAMPLE III

General Procedure for Extrusion

The pellets from Example II were extruded into a rod of approximately 0.05 inches in outer diameter. The average surface coefficient of friction of the extruded rod was determined to be 0.05, employing the procedure of Example V. A control polyurethane rod of similar dimensions showed an average surface coefficient of friction of 0.54.

The extrusion conditions employed were as follows:

| Extruder | Brabender ¾ inch |
|---|---|
| Temperature, °C. | Zone 1 127 |
| | Zone 2 150 |
| | Zone 3 175 |
| | Die 175 |
| Screw RPM (Setting) | 12 |
| Extruder Torque | 175 |
| Puller Speed | 30 |
| Air Gap | 1¼ inches |

EXAMPLE IV

General Procedure for Coextrusion

A melt of a thermoplastic polyurethane base polymer in a main extruder and a melt of the composition of Example II in a coextruder are maintained separately until combined in the forward, down stream portion of an extruder head. From the extruder head, the stream subsequently passes through and emerges from a tubing die (coaxial or cross head) as an integral tubing member having the composition laminated on a surface of the base polymer tubing. An extrusion temperature of 350° to 400° F. is used.

By proper selection of extruders, coextruders and dies, a tubing may be obtained having a laminated layer of the composition coated on either or both of the outside and lumen surfaces of the base polymer tubing.

EXAMPLE V

Lubricity Testing

Surface coefficients of friction were determined using an Instron Universal Testing Machine, Model 1122, and the drag generated between the sample and a natural rubber substrate was measured. Test samples were secured in a water filled trough and were soaked for 5 minutes before testing. A piece of clean natural pure gum rubber (lab grade, Fisher Scientific) was placed in contact with the test sample under water and pulled at a constant speed (5 cm/min) under a standard applied load (532 gm). The measured drag force in newtons (N) was converted to the coefficient of friction (CF) using the following equation:

$$CF = \frac{\text{Drag Force } (N) - \text{Internal Friction } (N)}{0.0098 \, (N/\text{gm}) \times \text{Applied Load (gm)}}$$

What is claimed is:

1. A method for preparing a shaped medical article comprising coextruding a melt of a substrate polymer and a melt of a coating composition comprising polyvinylpyrrolidone and a base polyurethane to give a shaped article of said substrate polymer having thereon a layer of said coating composition, said layer when wet absorbinq water and becoming lubricious.

2. The method of claim 1 wherein said substrate polymer is selected from the group consisting of polyvinylchloride, polyester, polyamide, polyacrylate, polystyrene, latex rubber and polyurethane.

3. The method of claim 1 wherein said polyvinylpyrrolidone is from 1 to 70% by weight of said composition.

4. The method of claim 1 wherein said article is a rod.

5. The method of claim 1 wherein said article is a tubing.

6. The method of claim 1 wherein said polyurethane is a polyetherpolyurethane.

7. The method of claim 1 wherein said layer is about 2.5 to 125 μ thick.

8. The method of claim 1 wherein said polyvinylpyrrolidone has a molecular weight of about 10,000 to 1,000,000.

9. A method for preparing a shaped medical article comprising melt fabricating a composition including polyvinylpyrrolidone and a thermoplastic base polymer to give a shaped article which absorbs water and becomes lubricious when wet.

10. The method of claim 9 wherein said fabricating is molding.

11. The method of claim 9 wherein said fabricating is extruding.

12. The method of claim 9 wherein said fabricating is coextruding said composition with a thermoplastic substrate polymer.

13. The method of claim 9 wherein said fabricating is extrusion coating said composition onto a surface of a shaped polymeric medical article.

14. A method for preparing a shaped medical article comprising:
a) preparing a homogeneous solution comprising a polyetherpolyurethane and polyvinylpyrrolidone in a solvent;
b) removing said solvent to leave a homogeneous blend of a coating composition comprising said polyetherpolyurethane and polyvinylpyrrolidone; and
c) coextruding said composition and a thermoplastic substrate polyurethane to give a shaped article of said substrate polyurethane having thereon a layer of said composition, said layer when wet absorbing water and becoming lubricious.

15. The method of claim 14 wherein said solvent is selected from the group consisting of dimethylformamide, dimethylacetamide, N-methylpyrrolidone, and mixtures thereof with a second solvent selected from the group consisting of tetrahydrofuran, methylene chloride and methylethylketone.

16. The method of claim 13 wherein the ratio of said polyetherpolyurethane and said polyvinylpyrrolidone in said solution is about 90:10 to 30:70.

* * * * *